United States Patent [19]

McGuire

[11] Patent Number: 5,093,969

[45] Date of Patent: Mar. 10, 1992

[54] SELF CONTAINED VISCERA TREATMENT UNIT

[76] Inventor: Lynne T. McGuire, 5743 26th St., NW., Washington, D.C. 20015

[21] Appl. No.: 642,754

[22] Filed: Jan. 18, 1991

[51] Int. Cl.⁵ .............................. A61G 17/00
[52] U.S. Cl. ........................... 27/21.1; 27/23.1
[58] Field of Search .............. 27/21.1, 23.1, 28; 452/106

[56] References Cited

U.S. PATENT DOCUMENTS

| | | | |
|---|---|---|---|
| 300,989 | 6/1884 | Lovett | 27/23.1 |
| 328,577 | 10/1885 | Ensworth | 27/23.1 |
| 1,058,551 | 4/1913 | Clark | 27/21.1 |
| 1,522,282 | 1/1925 | Beach et al. | 27/23.1 |
| 1,960,392 | 5/1934 | Ormsbee | 27/23.1 X |
| 2,446,930 | 8/1948 | Hower | 27/21.1 |
| 3,458,910 | 8/1969 | Ritchey | 27/21.1 |
| 4,901,410 | 2/1990 | Fischer et al. | 27/21.1 |
| 4,982,481 | 1/1991 | Deutscher | 27/21.1 |

Primary Examiner—Richard E. Chilcot, Jr.
Attorney, Agent, or Firm—Kenyon & Kenyon

[57] ABSTRACT

A method and apparatus for the direct treatment of viscera. The apparatus comprises an outer container, an inner container and a locking lid. The viscera are placed in the inner container, which is an open, perforated basket. The appropriate chemicals are poured over the viscera and the lid is locked into place. After treatment, the viscera are drained and stored until replaced into the human remains. The self contained viscera treatment unit may also be used to a containment vessel for drainage from contaminated or infectious bodies.

8 Claims, 2 Drawing Sheets

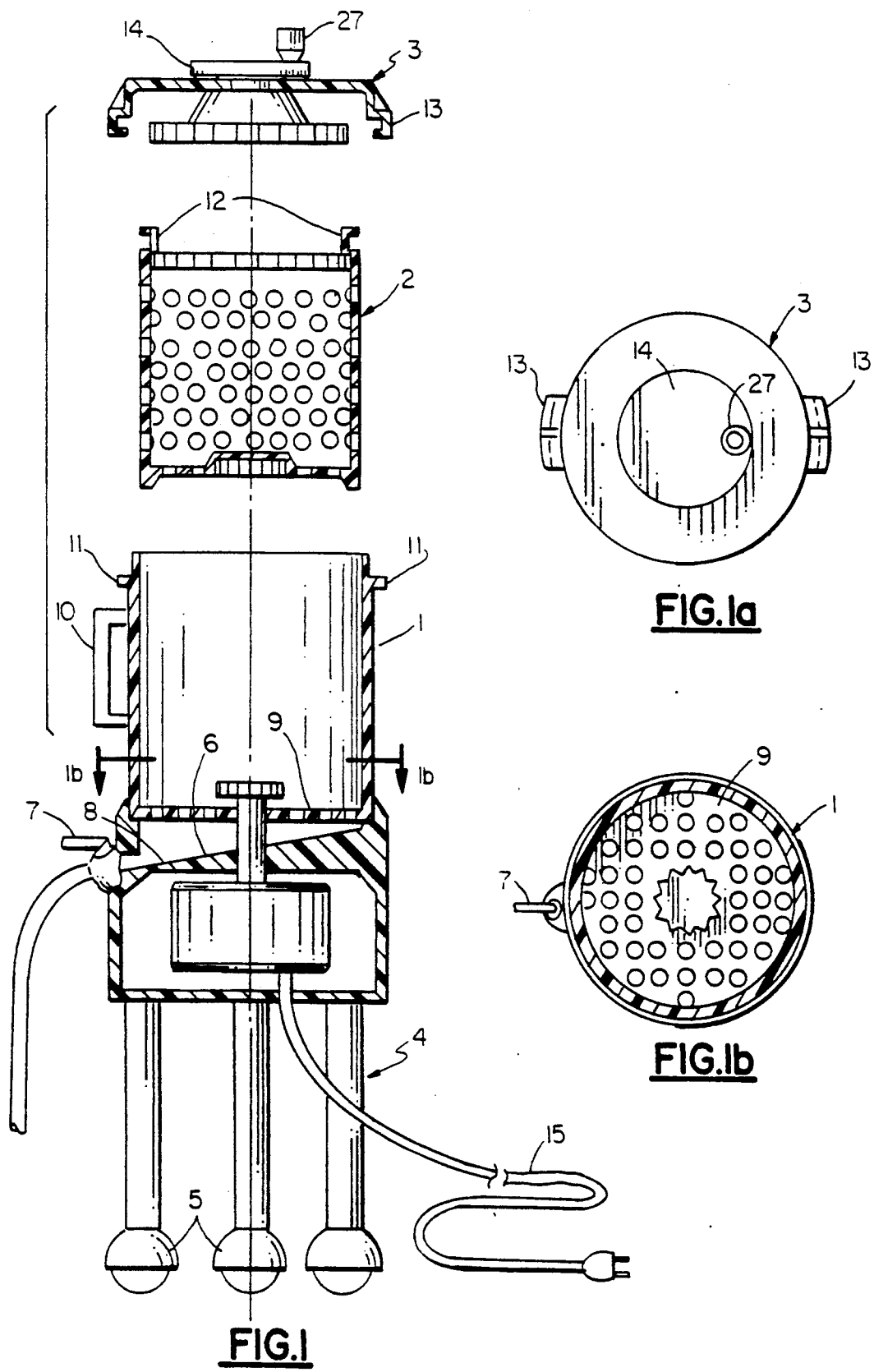

SELF CONTAINED VISCERA TREATMENT UNIT

FIELD OF THE INVENTION

This invention relates to a method and apparatus for treating, storing and draining viscera, which is particularly adapted for use where an autopsy has been performed on human remains, thus necessitating direct treatment of the viscera. More specifically, this invention relates to a self-contained viscera treatment unit, which may also be used as a containment unit for treated viscera, prior to replacement into the body, and for collecting and treating contaminated visceral drainage.

BACKGROUND OF THE INVENTION

Presently there are two methods for treating human viscera from autopsied bodies. In the first method, the viscera is placed in a cavity/viscera bag, typically made of heavy duty polyethylene, and embalming fluid is poured over the viscera and the mouth of the bag is closed, often with ligature/suture thread. The viscera are then set aside until arterial embalming of the body is complete and the body cavity and sidewalls have been thoroughly treated. Then the closed bag containing the viscera and embalming fluid is replaced into the body cavity and the body cavity is sutured and sealed.

In the second method, the viscera is placed into a large bucket or pail and embalming fluid is poured over the viscera. The bucket containing the viscera is then set aside and allowed to stand until arterial embalming of the body is complete and the body cavity and sidewalls are thoroughly treated. Then the viscera are individually removed from the bucket and placed into the body cavity. An alternative to individually placing the viscera into the body cavity is to remove them from the bucket and place them into a cavity/viscera bag, which is then placed into the body cavity.

A major problem associated with handling autopsied remains is leakage of embalming and cavity fluids, which can soil the garments on the autopsied body and make handling the autopsied remains unpleasant. Leakage of fluids can occur when either of the present methods of treating viscera are employed. With the first method, i.e., when the viscera/cavity bag is placed into the body cavity, fluids from the organs, as well as excess embalming fluid and air, are trapped in the cavity/viscera bag. Once the viscera bag is placed in the body cavity, the sternum, which is usually removed prior to removal of the viscera, is replaced. However, replacement of the sternum often punctures the viscera bag releasing the fluids into the body cavity. Often this released fluid seeps through the incisions which were made to autopsy the body or to remove the viscera.

When viscera are transferred directly to the body cavity, as in the second method, embalming fluids and semi-solid body tissue, may also be transferred to the body cavity. As more viscera are added, the excess fluid and other tissue transferred to the body cavity increases. The extra fluid may then seep through the incisions.

Apparatus for handling and treating viscera are known. U.S. Pat. No. 3,458,910 discloses an apparatus and a method for handling viscera. The apparatus of the '910 patent includes a tray, a plastic bag and a bucket. The plastic bag is placed the bucket and the tray is located in an inclined position over the opening of the bag. The method of the '910 patent comprises placing the viscera in the bag, closing the bag and replacing the bag containing the viscera into the body cavity. The '910 patent also teaches placing in the bag of certain fluids used in the embalming process. Further, the '910 patent teaches washing the viscera inside of the bag.

U.S. Pat. No. 4,901,410 discloses a cadaver preparation station comprising a tray having drain holes. The tray is placed on a tray support that also contains an air exhaust system. The apparatus of the '410 patent can be constructed so that it uses a fluid flush system on the tray.

Neither of the above-mentioned patents teaches or suggests a method for treating, storing or draining viscera. Nor does either patent disclose a self-contained viscera treatment unit, which can further be used to store and drain viscera prior to replacement into the autopsied body and to treat and collect contaminated viscera drainage. In fact, such a self-contained viscera treatment units and/or methods are not currently available in the field of funeral service. Therefore, there is a need to provide, inter alia, method and apparatus for treating human viscera, a containerized method for viscera submersion and drainage, a method and apparatus for collecting and treating contaminated drainage and a method of final viscera transfer.

SUMMARY OF THE INVENTION

The self contained viscera treatment unit of the present invention allows for the treatment and storage of the organs with appropriate chemical fluids while the embalming of the human remains is in progress. Further, upon completion of treatment, the viscera can be drained of the excess cavity and organic fluids, which greatly reduces the possibility of fluid leakage after the viscera is replaced into the body. The viscera treatment apparatus and method of the present invention also permits the use on the viscera of various additives, including hardening compounds.

The self contained treatment unit of the present invention may also be used to collect and contain visceral drainage prior to its disposal. Presently, visceral drainage is usually gathered in open sinks or urinals. A disinfectant or suitable pathogen inactivator is poured into the receptacle prior to disposal of the fluid. The self contained treatment unit of the present invention allows for the collection and treatment of such drainage in a less hazardous environment. The method and apparatus of the present invention is particularly useful when radioactive drainage must be stored for suitable decay before discharging.

The method and apparatus of the present invention also allows for the containment of the fluid vapors. If the lid of the apparatus is properly fastened, the fluid vapors become concentrated in the treatment unit, thus promoting the further penetration of viscera by preservative chemicals. Perhaps, more importantly, the containment of the vapors within the treatment unit may allow for compliance with environmental safety standards related to the concentration of certain chemicals in the atmosphere of the workplace.

BRIEF DESCRIPTION OF THE DRAWINGS

FIG. 1 is a schematic drawing of the electric version of the self contained viscera treatment unit constructed according to an embodiment of the invention.

FIG. 1a is a top-down view of the electric unit with locking lid closed.

FIG. 1b is a top-down view of the superior floor of the outer container of the electric unit.

DETAILED DESCRIPTION

Figures 2, 2A, 2B:
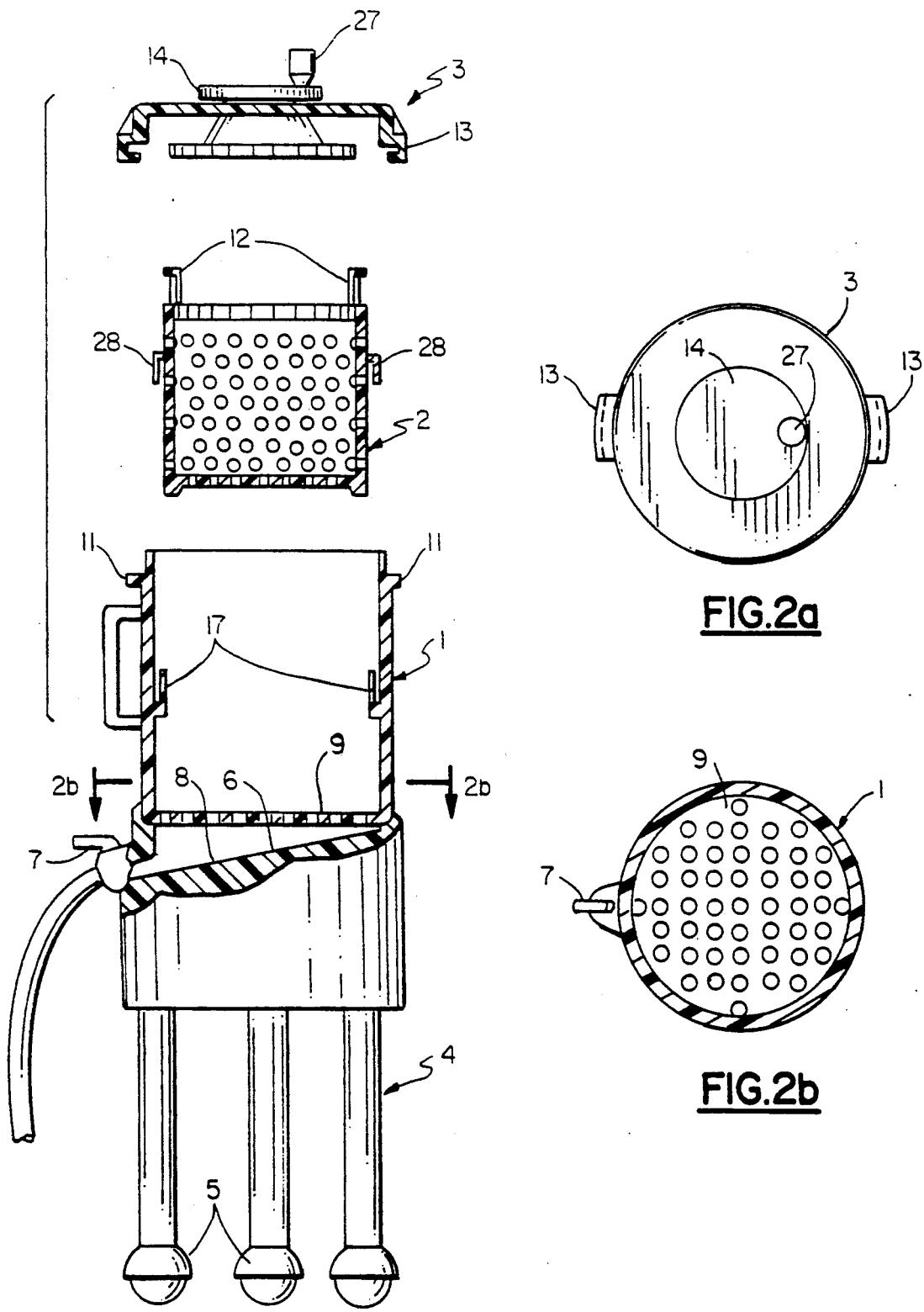
FIG. 2 is a schematic drawing of the manual drip version of the self contained viscera treatment unit constructed according to an embodiment of the invention.
FIG. 2a is a top-view of the manual unit with the locking lid closed.
FIG. 2b is a top-down view of the superior floor of the outer container of the manual drip unit.

The viscera treatment unit of the present invention comprises an outer container 1, an inner container 2, and a locking lid 3, all resting on an elevated stand 4 with locking wheels 5.

The outer container has an approximate capacity of 5–8 gallons, has a floor 6 of varying depth and has an outside drainage valve 7 having a shut-off lever. The inferior floor 8 of the body is slanted to facilitate the flow of fluids out through the drainage valve. The superior floor 9 contains perforations. There is an external handle 10 on the outer container for maneuvering the unit. The upper end of the outer container has laches 11 for the locking lid.

The inner container is a perforated basket having a set of handles 12 on the upper end to facilitate its removal from the outer container. The locking lid has a locking mechanism 13 for locking the lid onto the latches 11.

The self-contained viscera treatment unit can be constructed as either an electric or a manual drip unit. Both units provide for the treatment of organs from autopsied bodies with appropriate preservative chemicals. The lid of either embodiment of the viscera treatment unit can be locked to permit maximum penetration of the viscera by the preservative chemicals. Moreover, both units provide for the storage of treated viscera until they are ready for replacement into the autopsied body.

Differences between the electric unit and the manual drip unit relate to the drainaqe of the viscera. Along with the features described above, the electric unit has a power cord 15 for connection to a power source. The superior floor of the outer basket 16 of the electric unit is a spinning disk containing perforations. A calibrated spinning attachment 14, which allows for manual spinning, is optionally located on the lid of the electric unit. A knob 27 located on the lid is mechanically connected to the calibrated spinning attachment. Additionally, on the bottom of the inner basket of the electric unit, there are four guide/placement pegs which fit into the recesses of the spinning disk to help facilitate and maintain spinning.

In the second embodiment of the invention, i.e., the manual drip unit, drainage of the viscera occurs in a different manner. On the interior wall of the outer container of the manual drip unit there are two latches 17 onto which the inner container will hook when draining of the viscera is desired. On the exterior wall of the inner container there are two hooks 28 which fit into the latches located on the interior wall of the container body. These hooks and latches allow the inner container to be lifted out of the preservative chemicals, while still being contained within the viscera treatment unit. Additionally, the locking lid has central handle for easy removal of the lid.

When the viscera are ready for replacement into the body, they are first drained of excess fluids. Drainage is accomplished by first opening the drain valve of the viscera treatment unit. If the electric unit is used, the power is turned on to begin the spinning, and the viscera are spun for the desired time. If the electric unit is being used, but manual drainage of the viscera is desired, the calibrated spinning attachment should be placed onto the top of the inner container. The lid is then replaced and the external knob of the calibrated spinning attachment is used to spin drain the viscera in the inner container for the desired amount of time. Once the spinning is complete, the lid of the unit is removed as well as the inner container, and the viscera is replaced into the body cavity.

If the manual drip unit is being used and draining is desired, the lid of the unit is removed and the inner container is lifted so that the exterior hooks of the inner container fit securely into the latches on the inner wall of the outer container. The lid is then replaced and drainage begins. When drainage is complete, the lid is removed, the inner basket is removed and the viscera is replaced into the body cavity.

Either the electric or the manual unit can be used to collect drainage from contagious or infectious bodies. When the unit is being used as such, i.e., as a containment facility, the unit is positioned beneath a cadaver table drain or at the exit end of tubing which is connected to a vein tube that is used for draining a body. The drainage from either the table drain or the vein tube is treated with an appropriate disinfectant and is contained until it can be disposed.

While the invention has been described with reference to specific embodiments, it will be apparent to those skilled in the art that many alternatives, modifications, and variations may be made. Accordingly, it is intended to embrace all such alternatives, modifications that may fall within the spirit and scope of the appended claims.

What is claimed:

1. An apparatus for treating viscera comprising:
   a. an outer container resting on locking wheels, said outer container having
      i. an open upper end,
      ii. a floor having a drainage valve with a shut-off lever to the outside of said outer container wherein said floor is of varying depth such that the inferior edge of the floor is slanted to facilitate the flow of fluids out through the drainage valve and the superior edge of the floor is perforated, and
      iii. a handle located externally on the outer container;
   b. a perforated inner container capable of being placed within said outer container, said inner container having
      i. a handle attached thereto, and
      ii. an open upper end;
   c. a lid having a handle; and
   d. means for locking said lid to said open upper end of said outer container.

2. The apparatus of claim 1 wherein
   a. said outer container further has
      i. a power cord for connection to a power source,
      ii. wherein said superior floor is modified to a spinning disk having recesses; and
   b. said inner container further has placement pegs that fit into the recesses of the spinning disk.

3. The apparatus of claim 2 wherein
   a. said inner container further has a calibrated spinning attachment for manual spinning; and b. said lid has an external knob connected to the calibrated spinning attachment such that turning said external knob spins the inner container.

4. The apparatus of claim 1 wherein
   a. said outer container further has latches located interiorly; and
   b. said inner container further has hooks located exteriorly such that said hooks fit into said latches of the outer container.

5. A method for treating viscera comprising the steps of:
   a. placing viscera from an autopsy body into a treatment unit containing preservative chemicals;
   b. draining or spinning the excess fluid from the viscera; and
   c. placing the viscera in the body cavity or a cavity bag.

6. A method according to claim 5 wherein said treatment unit is the apparatus for treating viscera of claim 1.

7. A method for collecting drainage from a contagious or infectious body comprising the steps of:
   a. placing a viscera treatment unit beneath a cadaver table drain or at the exit end of a vein tube;
   b. collecting the drainage from a body in the viscera treatment unit;
   c. treating the drainage with disinfectant; and
   d. discharging the treated drainage.

8. The method according to claim 7 wherein said treatment unit is the apparatus for treating viscera of claim 1.

* * * * *